US005952009A

United States Patent [19]
Neurath et al.

[11] Patent Number: 5,952,009

[45] Date of Patent: Sep. 14, 1999

[54] METHODS FOR PREVENTING THE TRANSMISSION OF OR TREATING PATIENTS INFECTED WITH HERPESVIRUS

[75] Inventors: Alexander Robert Neurath; Asim Kumar Debnath, both of New York; Shibo Jiang, Jackson Heights, all of N.Y.

[73] Assignee: New York Blood Center, New York, N.Y.

[21] Appl. No.: 08/703,925

[22] Filed: Aug. 28, 1996

Related U.S. Application Data

[63] Continuation-in-part of application No. 08/618,830, Mar. 20, 1996, abandoned.

[51] Int. Cl.[6] .................................................... A61K 35/20

[52] U.S. Cl. ............................ 424/535; 514/12; 514/21; 530/359; 530/360; 530/362; 530/363; 530/365; 530/370

[58] Field of Search ........................ 514/12, 21; 424/535; 530/359, 360, 362, 363, 365, 367

[56] References Cited

U.S. PATENT DOCUMENTS

| | | | |
|---|---|---|---|
| 4,585,656 | 4/1986 | Rosenthal et al. | 424/195 |
| 5,010,167 | 4/1991 | Ron et al. . | |
| 5,164,486 | 11/1992 | Tsunoo et al. . | |
| 5,256,412 | 10/1993 | Tsunoo et al. . | |
| 5,290,571 | 3/1994 | Bounous et al. . | |
| 5,456,924 | 10/1995 | Bounous | 514/12 |

FOREIGN PATENT DOCUMENTS

| | | |
|---|---|---|
| 327461 | 8/1989 | European Pat. Off. . |
| 568200 | 11/1993 | European Pat. Off. . |
| 584558 | 3/1994 | European Pat. Off. . |
| 2625902 | 7/1989 | France . |
| 92/15316 | 9/1992 | WIPO . |

OTHER PUBLICATIONS

Chemical Abstracts, vol. 105, No. 17, Oct. 27, 1986, Columbus, OH, abstract No. 148687, V. Siksnis et al., "Stabilization of Enzymes by their Chemical Modification with Cyclic Aromatic Acid Anhydrides", *Dokl. Akad. Nauk. SSSR,* vol. 288, No. 6, 1986 (1508–1512).

Chemical Abstracts, vol. 103, No. 23, Dec. 9, 1985, Columbus, OH, abstract No. 192648, R.J.M Parker & R.S. Hodges, "Photoaffinity Probes Provide a General Method to Prepare Peptide Conjugates from Native Protein Fragments", *J. Prot. Chem.,* vol. 3, No. 5–6, 1984 (479–489).

Ostresh, J.M., Husar, G.M., Blondelle, S.E., Dorner, B., Weber, P.A., and Houghten, R.A., "Libraries from libraries: Chemical Transformation of Combinatorial Libraries to Extend the Range and Repertoire of Chemical Diversity", *Proc. Natl. Acad. Sci. USA,* 91, 11138–11142 (1994).

Abraham, R., Singh, N., Mukhopadhyay, A., Basu, S.K., Bal, V., and Rath, S., "Modulation of Immunogenicity and Antigenicity of Proteins by Maleylation to Target Scavenger Receptors on Macrophages", *J. Immunol.,* 154, 1–8 (1994).

Lo, T.W.C., Westwood, M.E., McLellan, A.C., Selwood, T. and Thornalley, P.J., "Binding and Modification of Proteins by Methylglyoxal Under Physiological Conditions. A Kinetic and Mechanistic Study with Nα–Acetylarginine, Nα–Acetylcysteine, and Nα–Acetyllysine, and Bovine Serum Albumin", *J. Biol. Chem.,* 269, 32299–32305 (1994).

Westwood, M.E., McLellan, A.C., and Thornalley, P.J., "Receptor–mediated Endocytic Uptake of Methylglyoxal–modified Serum Albumin. Competition with Advanced Glycation End Product–modified Serum Albumin at the Advanced Glycation End Product Receptor", *J. Biol. Chem.,* 269, 32293–32298 (1994).

McKenzie, H.A., "Whole casein: Isolation, Properties, and Zone Electrophoresis", In: *Milk Proteins Chemistry and Molecular Biology,* vol. II., H.A. McKenzie (ed.), pp. 87–116. Academic Press, New York (1971).

Jansen, R.W., Molema, G., Pauwels, R., Schols, D., DeClercq, E. and Meijer, D.K.F., "Potent In Vitro Anti–Human Immunodeficiency Virus–1 Activity of Modified Human Serum Albumins", *Molecular Pharmacology,* 39, 818–823 (1991).

Takami, M., Sone, T., Mizumoto, K., Kino, K., and Tsunoo, H., "Maleylated Human Serum Albumin Inhibits HIV–1 infection in Vitro", *Biochem. Biophys. Acta.,* 1180, 180–186 (1992).

Muckerheide, A., Apple, R.J., Pesce, A.J. and Michael, J.G., "Cationization of Protein Antigens", I. Alteration of Immunogenic Properties, *The Journal of Immunology,* 138, 833–837 (1987).

Suzuki, T., Burlingame, R.W., Cavalot, F., Andres, G., Kashiwazaki, S. and Tan, E.M., "Antibodies in Rabbits Immunized with Cationized IgG React with Histones H3 and H4", *Arthritis and Rheumatism,* 35, 1218–1226 (1992).

*Virology,* Fields, B.N., ed., Second Edition, Chapter 64, "Herpesviridae: A Brief Introduction", Bernard Roizman, 1787–1793 (1990).

Lundblad, R.L., *Chemical Reagents for Protein Modification,* 2nd Edition, CRC Press, Chapter 10, "The Modification of Lysine", 129–171 (1991).

(List continued on next page.)

*Primary Examiner*—Douglas W. Robinson
*Assistant Examiner*—Patrick R. Delaney
*Attorney, Agent, or Firm*—Frishauf, Holtz, Goodman, Langer & Chick, P.C.

[57] ABSTRACT

A method of preventing the transmission of or treating herpesvirus, such as herpes simplex virus infection, or Chlamydia trachomatis comprising administering to a patient a composition which comprises: (i) a protein or peptide containing lysines and an N-terminal amino group, wherein at least one of the lysines or the N-terminal amino group of the protein or peptide, such as casein, β-lactoglobulin, powdered milk or whey, is modified by contact with an aromatic acid anhydride compound, such as trimellitic anhydride, trimellitic anhydride chloride or 3-hydroxyphthalic anhydride and/or (ii) a protein or peptide containing arginines, which is modified by an arginine modifying agent containing at least one carboxyl group, such as p-carboxyphenylglyoxal.

11 Claims, 1 Drawing Sheet

OTHER PUBLICATIONS

Swart, P.J. and Meijer, D.K.F., "Negatively–charged Albumins: A Novel Class of Polyanionic Proteins with a Potent Anti–HIV Activity", *International Antiviral News,* 2, 69–71 (1994).

Kuipers, M.E., Huisman, J.G., Swart, P.J., de Béthune, M.–P., Pauwels, R., Schuitemaker, H., De Clercq, E. and Meijer, D.K.F., "Mechanism of Anti–HIV Activity of Negatively Charged Albumins: Biomolecular Interaction with the HIV–1 Envelope Protein gp120", *Journal of Acquired Immune Deficiency Syndromes and Human Retrovirology,* 11, 419–429 (1996).

Harmsen, M.C., Swart, P.J., de Bëthune, M.–P., Pauwels, R., De Clercq, E., The, T.H. and Meijer, D.K.F., "Antiviral Effects of Plasma and Milk Proteins: Lactoferrin Shows Potent Activity against Both Human Immunodeficiency Virus and Human Cytomegalovirus Replication In Vitro", *JID,* 172, 380–388 (1955).

Gordon, L.M., Waring, A.J., Curtain, C.C., Kirkpatrick, A., Leung, C., Faull, K. and Mobley, P.W., "Antivirals That Target the Amino–Terminal Domain of HIV Type 1 Glycoprotein 41", *AIDS Research and Human Retroviruses,* 11, 677–686 (1995).

Neyts, "Effect of Polyanionic on Vaginal Herpes" J. of Acquired Immune Deffic. Syndrome & Human Retrovirology v. 10, pp. 10–12, (1995).

Zaretsky, "Sulfated Polyanions Block *Chlamydia trachomatis"* Infection & Immunity, (Sep. 1995) v. 63, No. 9, pp. 3520–3526.

Zaretsky, "Sulfated Polyanions Block Chlampdia" (Abstract) Biosis #95: 439564 (1995).

Barnchez, "Anti–HIV Activity of Whey Portein" Teum Intl. Conference on AIDs (1994).

Tena–Quintero, "Virucidal Enzymic Milk Hydroxyzates" (1989) Caplus #1991: 49564.

Neyts, "Effects Polyanionic Compounds on Herpes & HIV" (1995) Caplus #1995: 942514.

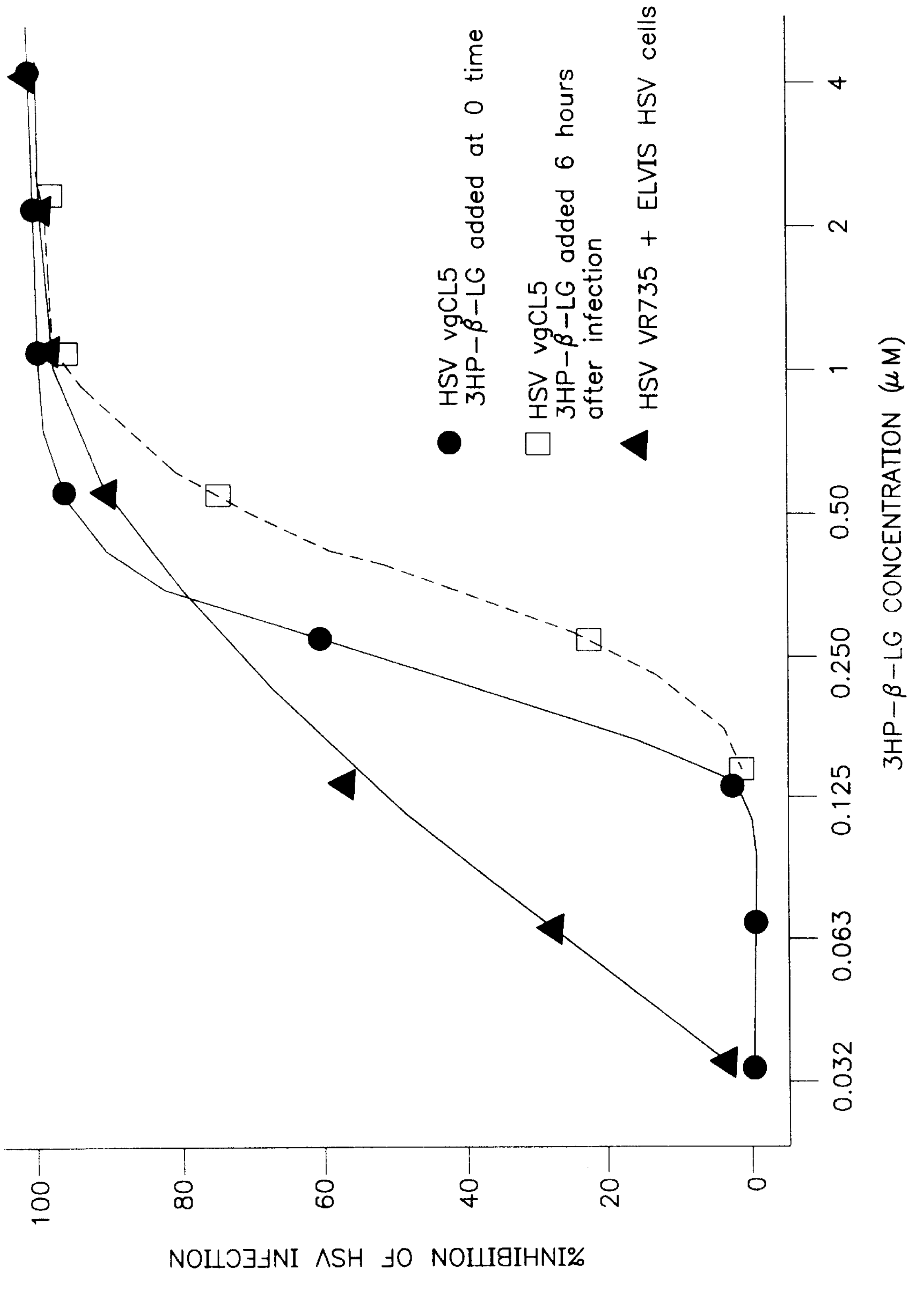
%INHIBITION OF HSV INFECTION
0
20
40
60
80
100
3HP-β-LG CONCENTRATION (μM)
0.032
0.063
0.125
0.250
0.50
1
2
4
HSV vgCL5
3HP-β-LG added at 0 time
HSV vgCL5
3HP-β-LG added 6 hours
after infection
HSV VR735 + ELVIS HSV cells

METHODS FOR PREVENTING THE TRANSMISSION OF OR TREATING PATIENTS INFECTED WITH HERPESVIRUS

RELATED APPLICATIONS

This application is a continuation-in-part application of application Ser. No. 08/618,830, filed Mar. 20, 1996 now abandoned.

This application is disallowed to related support matter in application Ser. No. 08/537,245, filed Sep. 29, 1995 (the entire contents of which are hereby incorporated by reference), which is a continuation-in-part application of application Ser. No. 08/492,940, filed Jun. 21, 1995 (now abandoned), which is a continuation-in-part application of application Ser. No. 08/420,573, filed Apr. 12, 1995 version abandoned.

GOVERNMENT RIGHTS

This invention was made with United States Government support under Grant CA 43315 from the National Institutes of Health. Accordingly, the United States Government has certain rights in this invention.

BACKGROUND OF THE INVENTION

1. Field of the Invention

The present invention concerns a method of preventing the transmission of herpesvirus or treating patients infected by herpesvirus and chlamydia trachomatis by administration of lysine-containing proteins or peptides modified by a lysine modifying agent, such as an aromatic acid anhydride compound, or arginine-containing proteins or peptides modified by an arginine modifying agent.

2. Background Information

Herpesviruses include the following viruses isolated from humans:

(1) herpes simplex virus 1 ("HSV-1")
(2) herpes simplex virus 2 ("HSV-2")
(3) human cytomegalovirus ("HCMV")
(4) varicella-zoster virus ("VZV")
(5) Epstein-Barr virus ("EBV")
(6) human herpesvirus 6 ("HHV6")
(7) herpes simplex virus 7 ("HSV-7")
(8) herpes simplex virus 8 ("HSV-8")

Herpesviruses have also been isolated from horses, cattle, pigs (pseudorabies virus ("PSV") and porcine cytomegalovirus), chickens (infectious larygotracheitis), chimpanzees, birds (Marck's disease herpesvirus 1 and 2), turkeys and fish (see "Herpesviridae: A Brief Introduction", *Virology,* Second Edition, edited by B. N. Fields, Chapter 64, 1787 (1990)).

Herpes simplex viral ("HSV") infection is generally a recurrent viral infection characterized by the appearance on the skin or mucous membranes of single or multiple clusters of small vesicles, filled with clear fluid, on slightly raised inflammatory bases.

The herpes simplex virus is a relatively large-sized virus. HSV-2 commonly causes herpes labialis. HSV-2 is usually, though not always, recoverable from genital lesions. Ordinarily, HSV-2 is transmitted venereally.

The time of initial herpes simplex virus infection is usually obscure except in the uncommon primary systemic infection occurring in infants and is characterized by generalized cutaneous and mucous membrane lesions accompanied by severe constitutional symptoms. Localized infections ordinarily appear in childhood, but may be delayed until adult life. It is presumed that the herpes simplex virus remains dormant in the skin and that herpetic eruptions are precipitated by overexposure to sunlight, febrile illnesses, or physical or emotional stress; also, certain foods and drugs have been implicated. In many instances, the trigger mechanism remains undetected.

The lesions caused by herpes simplex virus may appear anywhere on the skin or on mucous membranes, but are most frequent on the face, especially around the mouth or on the lips, conjunctiva and cornea, or the genitals. The appearance of small tense vesicles on an erythematous base follows a short prodromal period of tingling discomfort or itching. Single clusters may vary from 0.5 to 1.5 cm in size, but several groups may coalesce. Herpes simplex on skin tensely attached to underlying structures (for example, the nose, ears or fingers) may be painful. The vesicles may persist for a few days, then begin to dry, forming a thin yellowish crust. Healing usually occurs within 10 days after onset. In moist body areas, healing may be slower, with secondary inflammation. Healing of individual herpetic lesions is usually complete, but recurrent lesions at the same site may result in atrophy and scarring.

In females infected with HSV-2, there may be no skin lesions, the infection may remain entirely within the vagina. The cervix is frequently involved, and there is increasing evidence that this may be a factor in the development of carcinoma of the cervix.

Corneal lesions commonly consist of a recurrent herpetic keratitis, manifest by an irregular dendritic ulcer on the superficial layers. Scarring and subsequent impairment of vision may follow.

Gingivostomatitis and vulvovaginitis may occur as a result of herpes infection in infants or young children. Symptoms include irritability, anorexia, fever, inflammation, and whitish plaques and ulcers of the mouth. Particularly in infants, though some times in older children, primary infections may cause extensive organ involvement and fatal viremia.

In women who have an attack of HSV-2 late in pregnancy, the infection may be transmitted to the fetus, with the development of severe viremia. Herpes simplex virus may also produce fatal encephalitis.

Kaposi's varicelliform eruption (eczema herpeticum) is a potentially fatal complication of infantile or adult atopic eczema. Exposure of patients with extensive atopic dermatitis to persons with active herpes simplex should be avoided.

With respect of prophylaxis of HSV, in patients in whom sunlight is a precipitating factor, avoidance of overexposure and application of a sunscreen preparation is advisable.

No local or systemic chemotherapeutic agent has been demonstrated to be effective for treating herpes simplex virus with the possible exception of topical idoxuridine (IDU) in superficial herpetic keratitis. Reports on this compound in cutaneous herpes are conflicting. Other drugs which have been employed to treat HSV include trifluorothymidine, vidarabine (adenine arabinoside, ara-A), acyclovir, and other inhibitors of viral DNA synthesis may be effective in herpetic keratitis. These drugs inhibit herpes simplex virus replication and may suppress clinical manifestations. However, the herpes simplex virus remains latent in the sensory ganglia, and the rate of relapse is similar in drug-treated and untreated individuals. Moreover, some drug-resistant herpes virus strains have emerged.

The utilization of condoms may provide a degree of protection against transmission of HSV-2 infection during sexual intercourse, but a difficulty arises when condoms are not employed. Moreover, the use of condoms appears to be a culturally and socially unacceptable practice in many countries.

Although men may be able to protect themselves from HSV-2 infection by using condoms, women who are sexually active have no similar means. Women can encourage their male sex partners to use a condom, but may not succeed. The female condom, which is just becoming available, is expensive and there is presently no evidence that it prevents transmission of HSV-2.

Even maintaining a monogamous sexual relationship is no guarantee of safety, for if a woman's male partner becomes infected, he can pass the virus to her, and as more women are infected, so are more babies.

Diseases caused by varicella-zoster virus (human herpesvirus 3) include varicella (chickenpox) and zoster (shingles).

Cytomegalovirus (human herpesvirus 5) is responsible for cytomegalic inclusion disease in infants. There is presently no specific treatment for treating patients infected with cytomegalovirus.

Epstein-Barr virus (human herpesvirus 4) is the causative agent of infectious mononucleosis and has been associated with Burkitt's lymphoma and nasopharyngeal carcinoma.

Animal herpesviruses which may pose a problem for humans include B virus (herpesvirus of Old World Monkeys) and Marmoset herpesvirus (herpesvirus of New World Monkeys).

In an effort to expand the diversity of compounds with medically useful biological activities, the chemical transformation of synthetic peptide-based or other combinatorial libraries of organic compounds have been recently conceived (Ostresh, J. M., Husar, G. M., Blondelle, S. E., D örner, B., Weber, P. A., and Houghten, R. A., (1994), "Libraries from Libraries: Chemical Transformation of Combinatorial Libraries to Extend the Range and Repertoire of Chemical Diversity," *Proc. Natl. Acad. Sci. USA,* 91, 11138–11142). Such transformations can be accomplished with reagents which alter chemical moieties of library constituents in a defined manner and high yield. The diversity of compounds of interest to medicinal chemistry can be also increased by applying the concept of chemical modification to natural products, either in the form of mixtures of compounds or in the form of isolated individual components.

Site-specific chemical modification of amino acid residues in proteins has been widely used in structure/function studies in which a loss or decrease of biological activity was related to chemical modification of specific amino acid residues. Methods for covalent chemical modification of C, M, H, K, R, W, Y residues and carboxyl groups were described and applied to many proteins (Lundblad, R. C., (1991), *Chemical Reagents For Protein Modification,* CRC Press, Boca Raton, Fla.). In a few cases, it was reported that changes in net electric charge caused by chemical modification of proteins increased their activity ["cationized" protein antigens were reported to have increased or altered immunogenicity (Muckerheide et al., 1987; Suzuki et al., 1992)] or mimicked changes occurring during in vivo protein turnover, causing binding of the chemically modified proteins to scavenger receptors on cells, (Westwood, M. E., McLellan, A. C., and Thornalley, P. J., (1994), "Receptor-mediated Endocytic Uptake of Methylglyoxal-modified Serum Albumin. Competition with Advanced Glycation End Product-modified Serum Albumin at the Advanced Glycation End Product Receptor", *J. Biol. Chem.,* 269, 32293–32298; Lo, T. W. C., Westwood, M. E., McLellan, A. C., Selwood, T., and Thornalley, P. J., (1994), "Binding and Modification of Proteins by Methylglyoxal Under Physiological Conditions. A kinetic and Mechanistic Study with Nα-Acetylarginine, Nα-Acetylcysteine, and Nα-Acetyllysine, and Bovine Serum Albumin", *J. Biol. Chem.,* 269, 32299–32305; Abraham, R., Singh, N., Mukhopadhyay, A., Basu, S. K., Bal, V., and Rath, S., (1994), "Modulation of Immunogenicity and Antigenicity of Proteins by Maleylation to Target Scavenger Receptors on Macrophages," *J. Immunol.,* 154, 1–8).

Heretofore U.S. Pat. No. 5,164,486 and U.S. Pat. No. 5,256,412 (hereinafter collectively referred to as "Tsunoo et al") disclosed an anti-HIV agent comprising a plasma protein of which the polarity of at least one amino group was chemically modified into a negatively charged moiety by using aliphatic acid anhydrides. Tsunoo et al discussed treatment, not prevention of HIV infection, preferably by intravenous administration. Tsunoo et al mentioned maleic anhydride and succinic anhydride, but did not discuss aromatic acid anhydrides. The treated proteins blocked fusion of infected cells with uninfected cells by blocking HIV-1 mediated fusion. Tsunoo et al described plasma proteins such as human serum albumin, human immunoglobulin, human transferrin and human fibrinogen, but did not discuss milk, casein or whey.

Jansen et al (WO 92/15316) and "Potent In Vitro Anti-Human Immunodeficiency Virus-1 Activity of Modified Human Serum Albumins", *Molecular Pharmacology,* 39, 818–823 (1991)) described the use of cis-aconitic anhydride, propane-1,2,3-tricarboxylic acid anhydride, acetic anhydride, propionic anhydride, butyric anhydride, glutaric anhydride, phthalic anhydride, and maleic anhydride to modify protein and polypeptides from proteins such as albumin to prepare anti-viral pharmaceuticals, by imparting a negative charge to the proteins or polypeptides. The examples in WO 92/15316 were carried out only with aliphatic acid anhydrides.

However, to the best of applicants' knowledge, there have not been reported attempts of others to systematically modify protein amino acid residues of one or more kinds in order to: (1) generate compounds with medically important biological properties, of which the original protein was totally devoid; and (2) produce at the same time a compound (s) having the particular biological activity optimized.

Chlamydiae are a large group of obligate intra-cellular parasites closely related to gram-negative bacteria. They are divided into 2 species, Chlamydia psittaci and Chlamydia trachomatis, on the basis of antigenic composition, intracellular inclusions, sulfonamide susceptibility, and disease production.

C trachomatis produces compact intracytoplasmic inclusions that contain glycogen; it is usually inhibited by sulfonamides. It includes agents of mouse pneumonitis and several human disorders such as trachoma, inclusion conjunctivitis, nongonococcal urethritis, salpingitis, cervicitis, pneumonitis of infants, and lymphogranuloma venereum.

In endemic areas, sulfonamides, erythromycins, and tetracyclines have been used to suppress chlamydiae that cause eye infections. Periodic topical application of these drugs to the conjunctivas of all members of the community is sometimes supplemented with oral doses; the dosage and frequency of administration vary with the geographic area and the severity of endemic Trachoma. Drug-resistant C trachomatis has not been definitely identified except in laboratory experiments. Even a single monthly dose of 300 mg of doxycycline can result in significant clinical improvement, reducing the danger of blindness. Topical application of corticosteroids is not indicated and may reactivate latent trachoma. Chlamydiae can persist during and after drug treatment, and recurrence of activity is common.

It is believed that over 400 million people throughout the world are infected with trachoma and that 20 million are blinded by it. The disease is most prevalent in Africa, Asia, and the Mediterranean Basin, where hygienic conditions are poor and water is scarce. In such hyperendemic areas, childhood infection may be universal, and severe, blinding disease (resulting from frequent bacterial superinfections) is common. In the USA, trachoma occurs sporadically in some areas, and endemic foci persist on Indian reservations.

Control of trachoma depends mainly upon improvement of hygienic standards and drug treatment.

When socioeconomic levels rise in an area, trachoma becomes milder and eventually may disappear. Experimental trachoma vaccines have not given encouraging results. Surgical correction of lid defermities may be necessary in advanced cases.

*C trachomatis,* immunotypes D-K, is a common cause of sexually transmitted diseases that may also produce infection of the eye (inclusion conjunctivitis). In sexually active adults, particularly in the USA and western Europe—and especially in higher socioeconomic groups—*C trachomatis* is a prominent cause of nongonococcal urethritis and, rarely, epididymitis in males. In females, C trachomatis causes urethritis, cervicitis, salpingitis, and pelvic inflammatory disease. Any of these anatomic sites of infection may give rise to symptoms and signs, or the infection may remain asymptomatic but communicable to sex partners. Up to 50% of nongonococcal or postgonococcal urethritis or the urethral syndrome is attributed to chlamydiae and produces dysuria, non-purulent discharge, and frequency of urination.

This enormous reservoir of infectious chlamydiae in adults can be manifested by symptomatic genital tract illness in adults or by an ocular infection that closely resembles trachoma. In adults, this inclusion conjunctivitis results from self-inoculation of genital secretions and was formerly thought to be “swimming pool conjunctivitis.”

A neonate can acquire the infection during passage through an infected berth canal. Inclusion conjunctivitis of the newborn begins as a mucopurulent conjunctivitis 7–12 days after delivery. It tends to subside with erythromycin or tetracycline treatment, or spontaneously after weeks or months. Occasionally, inclusion conjunctivitis persists as a chronic chlamydial infection with a clinical picture indistinguishable from subacute or chronic childhood trachoma in nonendemic areas and usually not associated with bacterial conjunctivitis.

It is essential that chlamydial infections be treated simultaneously in both sex partners and in offspring to prevent reinfection.

Tetracyclines (eg, doxycycline, 100 mg/d by mouth for 10–20 days) are commonly used in non-gonococcal urethritis and in nonpregnant infected females. Erythromycin, 250 mg 4–6 times daily for 2 weeks, is given to pregnant women. Topical tetracycline or erythromycin is used for inclusion conjunctivitis, sometimes in combination with a systemic drug.

Genital chlamydial infection and inclusion conjunctivitis are sexually transmitted diseases that are spread by indiscriminate contact with multiple sex partners. Neonatal inclusion conjunctivitis originates in the mother’s infected genital tract. Prevention of neonatal eye disease depends upon diagnosis and treatment of the pregnant woman and her sex partner. As in all sexually transmitted diseases, the presence of multiple etiologic agents (gonococci, treponemes, Trichomonas, herpes, mycoplasmas, etc) must be considered. Instillation of 1% silver nitrate into the newborn’s eyes does not prevent development of chlamydial conjunctivitis. The ultimate control of this—and all sexually transmitted disease depends on reduction in promiscuity, use of condoms, and early diagnosis and treatment of the infected reservoir.

Adults with inclusion conjunctivitis often manifest upper respiratory tract symptoms (e.g., otalgia, otitis, nasal obstruction, pharyngitis), presumably resulting from drainage of infectious chlamydiae through the nasolacrimal duct. Pneumonitis is rare in Neonates infected by the mother may develop respiratory tract involvement 2–12 weeks after birth, culminating in pneumonia. There is striking tachypnea, paroxysmal cough, absence of fever, and eosinophilia. Consolidation of lungs and hyperinflation can be seen by x-ray. Diagnosis can be established by isolation of C trachomatis from respiratory secretions and can be suspected if pneumonitis develops in a neonate who has inclusion conjunctivitis. Systemic erythromycin (40 mg/kg/d) is effective treatment in severe cases.

Lymphogranuloma venereum (“LGV”) is a sexually transmitted disease, characterized by suppurative inguinal adenitis, that is common in tropical and temperate zones. The agent is *C trachomatis* of immunotypes L1--L3.

Untreated LGV infections tend to be chronic, with persistence of the agent for many years. Little is known about active immunity. The coexistence of latent infection, antibodies, and cell-mediated reactions is typical of many chlamydial infections.

The sulfonamides and tetracyclines have been used with good results to treat LGV, especially in the early stages. In some drug-treated persons there is a marked decline in complement-fixing antibodies, which may indicate that the infective agent has been eliminated from the body. Late stages require surgery.

LGV is most often spread by sexual contact, but not exclusively so. The portal of entry may sometimes be the eye (conjunctivitis with an oculoglandular syndrome). The genital tracts and rectums of chronically infected (but at times asymptomatic) persons serve as reservoirs of infection.

Although the highest incidence of LGV has been reported from subtropical and tropical areas, the infection occurs all over the world.

The measures used for the control of other sexually transmitted diseases apply also to the control of LGV. Case-finding and early treatment and control of infected persons are essential.

SUMMARY OF THE INVENTION

It is an object of the present invention to provide a method to prevent herpesvirus, such as herpes simplex virus infection.

It is a further object of the present invention to treat a patient infected with herpesvirus, such as herpes simplex virus.

It is an additional object of the present invention to prevent or treat a patient suffering from Chlamydia trachomatis.

The aforesaid objects are satisfied by the present invention.

The present invention concerns a method of preventing the transmission of herpesvirus, such as herpes simplex virus, and Chlamydia trachomatis and a method of treating a patient, such as an animal, e.g., a warm blooded animal, e.g., a human, that is infected with herpesvirus, such as herpes simplex virus, and Chlamydia trachomatis. Each of such methods involves administering a pharmaceutically anti-herpesvirus, or anti-Chlamydia trachomatis, effective amount of a composition (hereinafter sometimes referred to as "the composition for use in the present invention" or "active ingredient") comprising: (i) a protein or peptide containing lysines, wherein at least one, such as all or some, of the lysines and/or the N-terminal amino group of the protein or peptide is modified by contact with an aromatic acid anhydride compound and/or (ii) a protein or peptide containing arginines, wherein at least one arginine is modified by contact with an arginine modifying agent containing at least one carboxyl group, for example, p-carboxyphenylglyoxal. The composition may be administered alone or in combination with a pharmaceutically acceptable carrier (excipient or diluent).

The modified protein or peptide containing lysine, arginine or both, described above, can be administered after being treated with polyethylene glycol (PEG) ("PEGylation"). Since lysines and/or arginines are involved in chemical modifications in the compositions used in the present invention, the PEG can be linked to cysteine residues. Therefore the amount of PEG to be used depends on the amount of cysteine residues in the protein or peptides. The "PEGylated" modified proteins or peptides are candidates for anti-HSV agents for intravenous administration. The treatment with PEG can be carried out before or after the lysine or arginine residues of the protein or peptide are modified.

BRIEF DESCRIPTION OF THE DRAWING

The drawing (FIGURE) is a graph showing the inhibition of HSV infection as a function of the concentration of 3-hydroxyphthalic anhydride modified bovine β-lactoglobulin ("3HP-β-LG").

DETAILED DESCRIPTION OF THE INVENTION

Non-limiting examples of proteins or peptides which can be utilized in the present invention after being modified include proteins and peptides from animal or human sources, such as milk (such as powdered milk), whey, casein, egg albumin, egg white, ovomucoid, human serum albumin ("HSA"), bovine serum albumin ("BSA"), rabbit serum albumin, hemoglobin, poly-D-lysine, polyamidoamine dendrimers, alpha-lactalbumin and beta-lactoglobulin, preferably beta-lactoglobulin, whey, casein and powdered milk.

Beta-lactoglobulin ("β-LG") is the most abundant globular protein of milk and the major protein component of whey (2–4 g/l) (Phillips, L. G. Whitehead, D. M. and Kinsella, *J. Structure-function Properties of Food Proteins,* Academic Press, San Diego, (1994)). The safety of β-LG is explicit, since β-LG is consumed worldwide as a component of milk products (the worldwide production of whey is approximately 86 billion kg annually) (Morr, C. V. and Ha, E. Y. W., "Whey Protein Concentrates and Isolates: Processing and Functional Properties", *Critical Reviews in Food Science and Nutrition,* 33, 431–476 (1993)) and chemical modification does not substantially alter its antigenicity.

Low fat powdered milk containing about 80% casein (McKenzie, H. A., (1971), "Whole casein: Isolation, Properties, and Zone Electrophoresis", In: *Milk Proteins Chemistry and Molecular Biology,* Vol. II., H. A. McKenzie (ed.), pp 87–116. Academic Press, New York) as a protein or peptide mixture to be modified and then used in the present invention has the several following advantages: (1) preparations of chemically modified casein were difficult to sterilize by filtration (this problem did not occur with modified milk); (2) powdered milk is less expensive and more accessible than either BSA, HSA or casein; (3) both HSA and BSA would have to undergo virus inactivation processes in order to become licensed for human use. This problem does not arise with bovine milk and with milk-derived proteins such as casein and lactoglobulins.

The aromatic acid anhydride compound which modifies the protein or peptides for use according to the present invention includes compounds of the formula

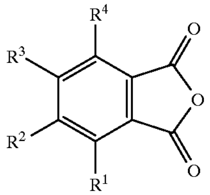

wherein $R^1$, $R^2$, $R^3$ and $R^4$ are independently H, —OH, —COOH, halogen or the group 0

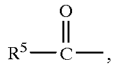

wherein $R^5$ is a halogen, and wherein at least one of $R^1$, $R^2$, $R^3$ and $R^4$ is not hydrogen.

The aromatic acid anhydride compound is preferably selected from the group consisting of trimellitic anhydride (1,2,4-benzenetricarboxylic anhydride), trimellitic anhydride chloride and 3-hydroxyphthalic anhydride.

Reagents that can be used for protein modification are listed hereinbelow in TABLE 1.

TABLE 1. List of Chemical Formulas of Reagents Used fo1 Protein Modification

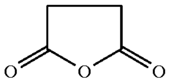

Succinic anhydride (1)

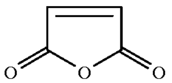

Maleic anhydride (2)

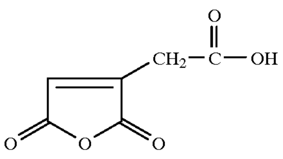

cis-Aconitic anhydride (3)

-continued

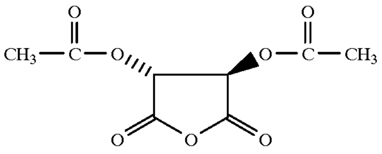

(+)-Diacetyl-L-tartaric anhydride (4)

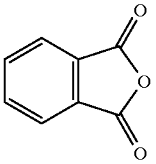

Phthalic anhydride (5)

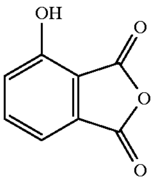

3-Hydroxyphthalic anhydride (6)

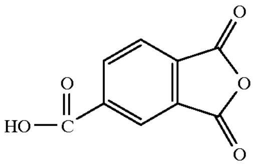

Trimellitic anhydride (7)

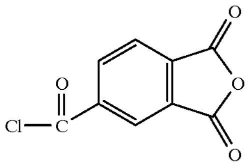

Trimellitic anhydride chloride (8)

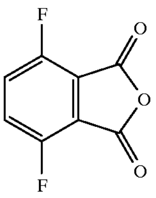

3,6-Difluorophthalic anhydride

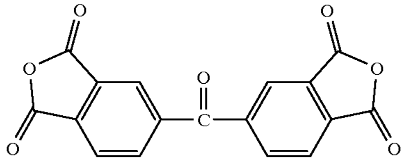

3,3',4,4'-Benzophenonetetracarboxylic dianhydride (10)

-continued

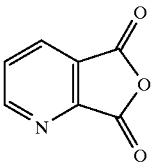

2,3-Pyridinedicarboxylic anhydride (11)

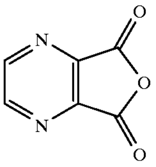

2,3-Pyrazinedicarboxylic anhydride (12)

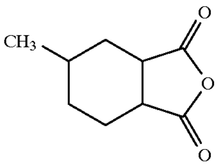

(±)-Hexahydro-4-methylphthalic anhydride (13)

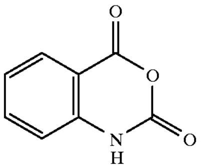

Isatoic anhydride (14)

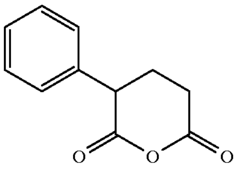

2-Phenylglutaric anhydride (15)

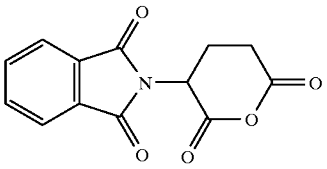

N-Phthaloyl-DL-glutamic anhydride (16)

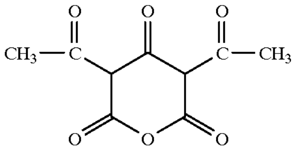

3,5-Diacetyltetrahydropyran-2,4,6-trione (17)

-continued

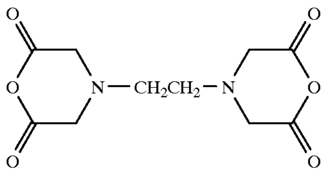

Ethylendiaminetetraacetic dianhydride (18)

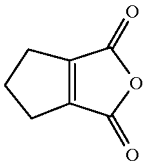

1-Cyclopentene-1,2-dicarboxylic anhydride (19)

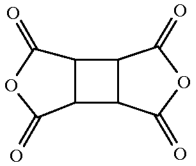

1,2,3,4-Cyclobutanetetracarboxylic dianhydride (20)

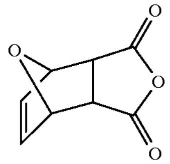

exo-3,6-Epoxy-1,2,3,6-tetrahydro-phthalic anhydride (21)

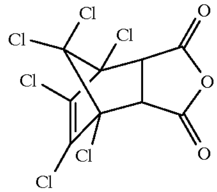

1,4,5,6,7,7-Hexachloro-5-norbornene-2,3-dicarboxylic anhydride (22)

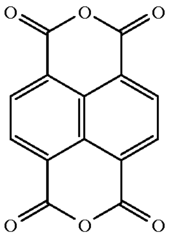

1,4,5,8-Naphthalene tetra-carboxylic acid dianhydride (23)

-continued

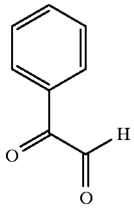

Phenylglyoxal (24)

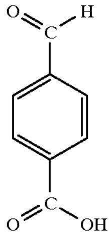

4-Carboxybenzaldehyde (25)

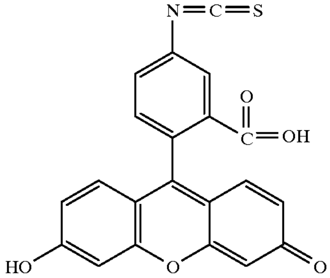

Fluorescein isothiocyanate (FITC) (26)

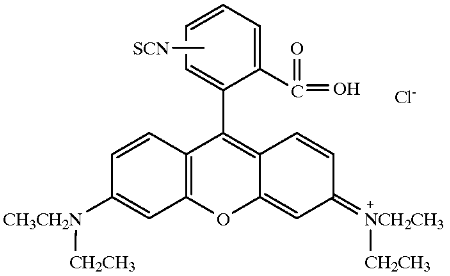

Rhodamine B isothiocyanate (27)

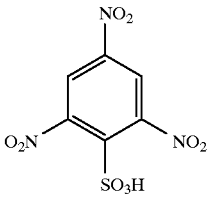

2,4,6-Trinitrobenzene sulfonic acid (28)

Chemically modified proteins for use in the present invention are listed hereinbelow in TABLE 2.

TABLE 2

| Chemically Modified Proteins |
|---|
| Trimellitic anhydride-BSA |
| Trimellitic anhydride-dendrimers |
| Phthalic anhydride-BSA |
| 1,4,5,8-Naphthalenetetracarboxylic dianhydride-BSA |
| Phenylglyoxal-BSA |
| Phthalic anhydride-phenylglyoxal-BSA |
| 3-Hydroxyphthalic anhydride-BSA |
| Phthalic anhydride-reduced and alkylated BSA |
| Phthalic anhydride-HSA |
| 1,4,5,8-Naphthalenetetracarboxylic dianhydride-HSA |
| Phthalic anhydride Rabbit Serum Albumin |
| Phthalic anhydride-Gelatin |
| Phthalic anhydride-Casein I |
| Phthalic anhydride-Casein II |
| Phthalic anhydride-phenylglyoxal-Casein |
| Phenylglyoxal-Casein |
| 3,3',4,4'-Benzophenonetetracarboxylic dianhydride-BSA |
| 1,2,3,4-Cyclobutanetetracarboxylic dianhydride-BSA |
| Trimellitic anhydride-HSA |
| 1,4,5,8-Naphthalenetetracarboxylic dianhydride-Gelatin |
| 1-Cyclopentene-1,2-dicarboxylic anhydride-BSA |
| Hexahydro-4-methylphthalic anhydride-BSA |
| 2-Phenylglutaric anhydride-BSA |
| 2,3-Pyrazinedicarboxylic anhydride-BSA |
| Isatoic anhydride-BSA |
| 3-Hydroxyphthalic anhydride-milk |
| 3-Hydroxyphthalic anhydride-Casein |
| cis-Aconitic anhydride-Casein |
| Trimellitic anhydride chloride-BSA |
| exo-3,6-Epoxy-1,2,3,6-tetrahydrophthalic anhydride-BSA |
| N-Phthaloyl-DL-glutamic anhydride-BSA |
| Trimellitic anhydride-phenylglyoxal-BSA |
| Trimellitic anhydride phenylglyoxal-HSA |
| 2,3-Pyridinedicarboxylic anhydride-BSA |
| Ethylenediaminetetracetic dianhydride-BSA |
| 3,6-Difluorophthalic anhydride-BSA |
| 1,4,5,6,7,7-Hexachloro-5-norbornene-2,3-dicarboxylic anhydride-BSA |
| 3,5-Diacetyltetrahydropyran-2,4,6-trione-BSA |
| Trimellitic anhydride-transferrin |
| Trimellitic anhydride-trypsin-treated-BSA |
| Trimellitic anhydride-IgG |
| 4-Carboxybenzaldehyde-BSA |
| Trimellitic anhydride-poly-D-Lysine |
| 2,4,6-Trinitrobenzene sulfonic acid-BSA |
| Fluoresceine-isothiocyanate (FITC)-BSA |
| Rhodamine B isothiocyanate-BSA |
| Trimellitic anhydride-Casein |
| Trimellitic anhydride chloride-Casein |
| Trimellitic anhydride-milk |
| Trimellitic anhydride chloride-milk |
| cis-Aconitic anhydride-milk |
| Maleic anhydride-milk |
| cis-Aconitic anhydride-phenylglycoxal-milk |
| 3-Hydroxyphthalic anhydride-phenylglyoxal-milk |
| Trimellitic anhydride chloride-HSA |
| 3-Hydrophthalic anhydride-α-lactalbumin |
| 3-Hydroxyphthalic anhydride-β-Lactoglobulin |
| 3-Hydroxyphthalic anhydride (1:1 mg/ml)-β-Lactoglobulin |
| 3-Hydroxyphthalic anhydride (5:1 mg/ml)-β-Lactoglobulin |
| PEGylated 3-Hydroxyphthalic anhydride-β-Lactoglobulin |
| 3-Hydroxyphthalic anhydride-Whey |
| 3-Hydroxyphthalic anhydride-Egg Albumin |
| 3-Hydroxyphthalic anhydride-Egg White |
| 3-Hydroxyphthalic anhydride-purified Ovomucoid |
| Trimellitic anhydride-β-lactoglobulin |
| Trimellitic chloride-β-lactoglobulin |
| Trimellitic anhydride-β-lactalbumin |
| Trimellitic chloride-α-lactalbumin |
| p-Carboxyphenylglyoxal-BSA |
| 1,2,4-Benzenetricarboxylic anhydride-β-Lactoglobulin |
| Trimellitic anhydride chloride-β-Lactoglobulin |
| 1,2,4-Benzenetricarboxylic anhydride-Hemoglobin |

A particularly preferred modified protein according to the present invention is bovine beta-lactoglobulin treated with 3-hydroxyphthalic anhydride (3HP-β-LG) or bovine beta-lactoglobulin treated with 1,2,4-benzenetricarboxylic anhydride (=trimellitic anhydride) or with trimellitic anhydride chloride.

The protein or peptide for use in the present invention may include a soy protein treated with a detergent (for example, sodium dodecyl sulfate (SDS); 10 mg/ml). Other detergents for treating a soy protein are listed hereinbelow.

TABLE 3

Detergents for Treating Soy Proteins

| CHEMICAL NAME OR TRADE NAME | CHEMICAL SYNONYMS |
|---|---|
| Big CHAP | N,N,bis (3-D-gluconamidopropyl) cholamide |
| BRIJ 35 | LAURETH-23<br>Polyoxyethylene (23) lauryl ether<br>$C_{12}E_{23}$ |
| $C_{12}E_8$ | Octaethylene glycol monododecyl ether<br>Octaethylene glycol monolauryl ether<br>Polyoxyethylene (8) lauryl ether |
| $C_{12}E_9$ | Nonaethylene glycol monododecyl ether<br>Nonoctaethylene glycol monolauryl ether<br>Polyoxyethylene (9) lauryl ether |
| Cetyltrimethylammonium bromide | CTAB<br>Centrimmonium bromide<br>Cetrimide |
| CHAPS | 3-[(3-Cholamidopropyl) dimethylammonio]-1-propanesulfonate |
| CHAPSO | 3-[(3-Cholamidopropyl) dimethylammonio]-2-hydroxypropane-1-sulfonate |
| Cholate, sodium | Cholic acid, monosodium salt<br>Sodium cholic acid |
| Decyl-β-D-glucopyranoside | Decyl glucoside |
| Decyl-β-D-maltopyranoside | Decyl maltoside |
| Deoxy Big CHAP | N,N-bis(3-D-gluconamidopropyl) deoxycholamide |
| Deoxycholate, sodium | Deoxycholic acid, sodium salt<br>Sodium deoxycholic acid |
| Digitonin | Digitin |
| Dodecyl-β-D-maltopyranoside | Dodecyl maltoside<br>Lauryl maltoside |
| Dodecyl sulfate, sodium | lauryl sulfate, sodium |
| EMPIGEN BB | N-Dodecyl-N,N-dimethylglycine<br>N-Lauryl-N,N-dimethylglycine |
| bis (2-Ethylhexyl) sodium sulfosuccinate | Dioctyl sodium sulfosuccinate; docusate sodium |
| GENAMINOX KC | Lauryldimethylamine oxide<br>Dodecyldimethylamine oxide<br>LDAO |
| GENAPOL C-100 | Polyoxyethylene (10) monolauryl ether<br>Decaoxyethylene monolauryl ether<br>Decaoxyethylene dodecyl ether |
| GENAPOL X-080 | Octaethylene glycol isotridecyl ether<br>Polyoxyethylene (8) isotridecyl ether |
| GENAPOL X-100 | Polyoxyethylene (10) isotridecyl ether<br>PEG (10) tridecyl ether |
| GENAPOL X-150 | Polyoxyethylene (15) isotridecyl ether<br>PEG (15) isotridecyl ether |
| Glycocholate, sodium | Glycocholic acid, sodium salt<br>Monosodium glycocholic acid |
| Glycodeoxycholate, sodium | Glycodeoxycholic acid, sodium salt |

TABLE 3-continued

Detergents for Treating Soy Proteins

| CHEMICAL NAME OR TRADE NAME | CHEMICAL SYNONYMS |
|---|---|
| Heptyl-β-D-glucopyranoside | Heptyl glucoside |
| Heptyl-β-D-thioglucopyranoside | Heptyl thioglucoside |
| Hexyl-β-D-glucopyranoside | Hexyl glucoside |
| Lauryldimethylamine oxide | Dodecyldimethylamine oxide<br>Dimethyllaurylamine oxide<br>N,N-Dimethyl-N-dodecylamine oxide<br>LDAO |
| Lauryl sulfate sodium | Sodium lauryl sulfate<br>Sodium dodecyl sulfate<br>SDS<br>SLS |
| LUBROL PX | Polyoxyethylene (9) lauryl ether<br>PEG (9) dodecyl ether<br>Polidocanol |
| MEGA-8 | OMEGA<br>Octanoyl-N-methylglucamide |
| MEGA-9 | Nonanoyl-N-methylglucamide |
| MEGA-10 | Decanoyl-N-methylglucamide |
| Nonyl-β-D-glucopyranoside | Nonyl glucoside |
| NP-40 | NONIDET P-40<br>Nonaethylene glycol octylphenyl ether<br>PEG (9) octylphenyl ether |
| Octy1-β-D-glucopyranoside | Octyl glucoside<br>OG |
| Octyl-β-D-thioglucopyranoside | Octyl thioglucoside<br>OSG |
| PLURONIC F-127 | Polyoxyethylene polyoxypropylene block copolymer<br>Polyethylene polypropylene glycol |
| Taurocholate, sodium | Taurocholic acid, sodium salt<br>Monosodium taurocholic acid |
| Taurodeoxycholate, sodium | Taurodeoxycholic acid, sodium salt<br>Sodium taurodesoxycholate |
| THESIT | $C_{12}E_9$<br>Nonaethylene glycol mono-dodecyl ether |
| TRITON X-100 | Nonaethylene glycol octylphenol ether<br>PEG (9) octylphenyl ether |
| TRITON X-100, Hydrogenated | RTX-100 |
| TRITON X-114 | Heptaethylene glycol octylphenyl ether<br>PEG (7) octylphenyl ether |
| TWEEN 20 | Polyoxyethylene sorbitan monolaurate<br>PEG (20) sorbitan monolaurate<br>POLYSORBATE 20 |
| TWEEN 80 | Polyoxyethylene sorbitan monoleate<br>PEG (20) sorbitan monoleate<br>POLYSORBATE 80 |
| ZWITTERGENT 3-08 | N-Octylsulfobetaine<br>3-(Octyldimethylammonio) propane-1-sulfonate<br>SB 3-08<br>SB08 |
| ZWITTERGENT 3-10 | N-Decylsulfobetaine<br>3-(Decyldimethylammonio) propane-1-sulfonate<br>SB 3-10<br>SB10 |
| ZWITTERGENT 3-12 | N-Dodecylsulfobetaine<br>3-(Dodecyldimethylammonio) propane-1-sulfonate<br>SB 3-12<br>SB10 |
| ZWITTERGENT 3-14 | N-Tetradecylsulfobetaine<br>3-(Docecyldimethylammonio) propane-1-sulfonate<br>SB 3-14<br>SB14 |
| ZWITTERGENT 3-16 | N-Hexadecylsulfobetaine<br>3-(Hexacecyldimethylammonio) propane-1-sulfonate<br>SB 3-16<br>SB16 |
| n-Dodecanoylsucrose | |
| octanoyl sucrose | |
| tetradecyl-beta-D-maltoside | |
| dimethyldioctadelyl ammonium bromide | |

It is preferred to add 0.1 to 100 grams and preferably 0.2 to 5 grams of the aromatic acid anhydride compound per gram of the protein or peptide dissolved in an appropriate buffer, e.g., a phosphate buffer or a carbonate buffer.

The contacting of the protein or peptide and the aromatic acid anhydride compound is preferably carried out at a temperature of 0° C. to 50° C., more preferably 15° C. to 30° C. for 15 to 720 minutes, more preferably for 30 to 180 minutes at a pH of 5 to 11, more preferably at a pH of 6 to 9.

The contacting of the protein or peptide containing arginines (such as egg albumin, egg white, ovomucoid, hemoglobin, human serum albumin, bovine serum albumin, rabbit serum albumin, casein, polyamidoamine, alpha-lactalbumin and beta-lactoglobulin) and the arginine modifying agent is preferably carried out at a temperature of 37° C. for 2 hours at a pH of 8.5.

The methods of the present invention can be used to prevent or treat all types of herpesvirus, in humans and animals. In humans, the present invention can be effective for treating or preventing HSV, such as HSV-1, HSV-2, HSV-7 and HSV-8, as well as human cytomegalovirus, varicella-zoster virus, Epstein-Barr virus and human herpesvirus 6. Preferred embodiments of the present invention are for preventing HSV-1, HSV-2, which is known to be transmitted sexually and HSV-8, which is known to be a causative agent of Kaposi's sarcoma.

In the methods of the present invention for preventing or treating herpesvirus infection, such as HSV infection or Chlamydia trachomatis, in a patient, i.e., an animal, for example, a warm-blood animal, for example, a human, a pharmaceutically effective anti-herpesvirus amount, or a pharmaceutically effective anti-Chlamydia trachomatis amount, of the modified protein or peptide described hereinabove is administered to a patient, i.e., an animal, for example, a warm-blood animal, for example, a human. Especially for prevention of herpesvirus infection, such as HSV infection, it is preferred that the composition for use in the present invention be administered to an appropriate region of the body of the patient, for example, the human body, and local administration is preferred in many situations.

The phrase "administration to an appropriate region of the body" includes, for example, application of the composition used in the present invention to regions of the body of the patient, for example, the region of the human body which comes into close contact with another human body, for example, application (directly or indirectly) to the male or female genitalia if the method is intended to prevent transmission of HSV-1 and HSV-2 or Chlamydia trachomatis during sexual intercourse, and application to the vagina or to a baby's epidermis if the method is intended to prevent transmission of HSV during childbirth.

The term "local administration" includes any method of administration in which the activity of the composition of the present invention is substantially confined to the region of the patient's body to which it is applied, i.e., vaginal, rectal or topical administration (for example, the aforesaid composition can be topically applied to HSV lesions,, such as lesions caused by herpes simplex virus, such as HSV-1, HSV-2, zoster or HSV-8).

The present invention thus provides a method of preventing herpesvirus infection which is transmitted by sexual contact, such as vaginal transmission of, for example, herpes simplex virus, such as HSV-1 and HSV-2 or preventing Chlamydia trachomatis, either during sexual intercourse or during childbirth (vaginal delivery), by vaginal administration, such as by administering a cream, ointment, lotion, jelly, solution, emulsion or foam formulation containing a pharmaceutically effective anti-HSV amount of the composition for use in the present invention, either alone or in combination with a pharmaceutically acceptable carrier, excipient or diluent.

The present invention also therefore relates to a method of preventing transmission of, for example, herpes simplex virus, such as HSV-1 and HSV-2 to a newborn baby by topically administering to the mother before childbirth and to the baby soon after childbirth a pharmaceutically effective anti-herpesvirus amount of the composition used in the present invention, either alone or in combination with a pharmaceutically acceptable carrier, excipient or diluent.

To prevent herpesvirus infection which is transmitted by sexual contact, the above described composition can be applied to a contraceptive device (for example, a male or female condom, a contraceptive diaphragm or a contraceptive sponge, for example, a polyurethane foam sponge), prior to sexual intercourse.

Alternatively, the composition described above can be applied on a pessary or tampon for vaginal administration.

The pharmaceutical formulation for topical administration would comprise a pharmaceutically effective anti-herpesvirus amount, or a pharmaceutically effective anti-Chlamydia trachomatis amount, of the composition of the present invention and at least one pharmaceutically acceptable topical carrier, excipient or diluent, to form an ointment, cream, gel, lotion, paste, jelly, spray or foam.

The amount of the active ingredient (composition) for use in the present invention will vary, not only with the particular modified proteins or peptides, but also with the route of administration, and the age and condition of the human to which the composition is administered and will be ultimately determined by the discretion of the attendant physician. In general, however, a suitable concentration of the composition in a topical dosage form is up to 40 milligrams per milliliter, preferably between 10 and 20 milligrams per milliliter.

While it is possible that the composition for use in the present invention ("active ingredient") may be administered as the raw composition, it is preferable to present the active ingredient in conjunction with a pharmaceutically acceptable excipient, diluent or carrier, as a pharmaceutical formulation.

The invention thus involves the use of a pharmaceutical formulation comprising the active ingredient together with one or more pharmaceutically acceptable carriers, excipients or diluents therefor and, optionally, other prophylactic ingredients. The carrier(s), excipient(s) or diluent(s) should be "acceptable" in the sense of being compatible with the other ingredients of the formulation and not deleterious to the recipient therefor.

Pharmaceutical formulations include those suitable for vaginal, oral, rectal, nasal or topical (including buccal and sub-lingual) administration. The formulations may, where appropriate, be conveniently presented in discrete dosage units and may be prepared by any of the methods well known in the art of pharmacy. All such methods include the step of bringing into association the active ingredient with liquid carriers or finely divided solid carriers or both and then, if necessary, shaping the product into the desired formulation.

Formulations suitable for vaginal administration may be presented as pessaries, tampons, creams, gels, pastes, jelly, foams or sprays or aqueous or oily suspensions, solutions or emulsions (liquid formulations) containing in addition to the active ingredient, such carriers as are known in the art to be appropriate. These formulations are useful to protect not only against sexual transmission of HSV, but also to prevent infection of a baby during passage through the birth canal. Thus the vaginal administration can take place prior to sexual intercourse, during sexual intercourse, immediately prior to childbirth or during childbirth.

As a vaginal formulation, the active ingredient may be used in conjunction with a spermicide and as discussed above, may be employed with condoms, diaphragms, sponges or other contraceptive devices.

Pharmaceutical formulations suitable for oral administration may conveniently be presented as discrete units such as capsules, cachets or tablets each containing a predetermined amount of the active ingredient; as a powder or granules; as a solution; as a suspension; or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspension, solutions, emulsions, syrups or elixirs, or may be presented as a dry product for constitution with water or other suitable vehicle before use.

Depending on the protein employed in the composition which is administered, the composition according to the present invention may be administered intravenously, for example, when PEGylated proteins or a treated hemoglobin are employed.

Although the dosage may vary depending on several factors, such as the age of the patient and the route of administration, in the case of oral administration to an adult human patient, the composition for use in the present invention may normally be administered at a total daily dose of 1 to 5000 mg, preferably from 5 to 300 mg, in a single dose or in divided doses. In the case of intravenous administration, the dose may be 0.1 to 100 mg and preferably 0.5 to 30 mg, with the dose being administered one to three times a day.

The composition of the present invention can also be employed as a food additive to inhibit the spread of the herpesvirus or Chlamydia trachomatis in the intestinal tract and possibly at other sites.

Liquid preparations for oral or vaginal administration may contain conventional additives such as suspending agents, emulsifying agents, non-aqueous vehicles (which may include edible oils) or preservatives.

For topical administration to the epidermis, the active ingredient may be formulated as an ointment, cream, paste, jelly, foam, gel or lotion, or as a transdermal patch for topical administration. Ointments, pastes, jellies, liquids, foams, gels and creams may, for example, be formulated with an aqueous or oil base with the addition of suitable thickening and/or gelling agents. Lotions may be formulated with an aqueous or oil base and will in general also contain one or more emulsifying agents, stabilizing agents, suspending agents, thickening agents, or coloring agents. Such topical dosage forms may be particularly useful when applied to a newborn baby of an HIV-infected mother.

Formulations suitable for topical administration in the mouth include lozenges comprising an active ingredient in a flavored base, usually sucrose and acacia or tragacanth; or pastilles comprising the active ingredient in a suitable liquid carrier.

Pharmaceutical formulations suitable for rectal administration, wherein the carrier is a solid, are most preferably represented as unit dose suppositories. Suitable carriers include cocoa butter and other materials commonly used in the art, and the suppositories may be conveniently formed by admixture of the active compound with the softened or melted carrier(s) followed by chilling and shaping in molds.

Drops may be formulated with an aqueous or non-aqueous base comprising one or more dispersing agents, solubilizing agents or suspending agents. Liquid sprays are conveniently delivered from pressurized packs.

When desired, the above described formulations adapted to give sustained release of the active ingredient may be employed.

The pharmaceutical compositions for use according to the invention may also contain other active ingredients such as spermicides as discussed above, or antimicrobial agents, preservatives or other anti-viral agents.

EXAMPLES

The present invention will now be described with reference to the following non-limiting examples.

Reagents

The following macromolecular compounds can be used for chemical modifications (sources are given in parentheses): Bovine serum albumin ("BSA"), human transferrin, casein and poly-D-lysine (M.W. 60,000) (Sigma, St. Louis, Mo.); beta-lactoglobulin (3×crystallized) from bovine whey (Sigma); human serum albumin (HSA) and IgG (The New York Blood Center, New York); gelatin (Bio-Rad Laboratories, Richmond, Calif.); polyamidoamine dendrimers (72Å diameter, M.W. 58,000; Polysciences Inc., Warrington, Penn.); and Carnation non-fat dry milk powder (34.8% protein; local supermarket). Fluorescein isothiocyanate (FITC) and rhodamine B isothiocyanate modified BSA, respectively, can also be obtained from Sigma.

Reagents for modification of lysine and arginine residues, such as 3-hydroxyphthalic anhydride, listed in TABLE 2 herein, can be obtained from Aldrich, Milwaukee, Wis., except for FITC which can be obtained from Molecular Probes, Eugene, Oreg.

Example 1

Chemical modification of proteins and other macromolecules

The compounds such as beta-lactoglobulin were dissolved in 0.1 M phosphate pH 8.5 at a final concentration of 20 mg/ml. Acid anhydrides (see TABLE 1 herein) were dissolved in dimethylformamide (or dimethysulfoxide) at the highest possible concentration, for example, 200 mg/ml. Aliquots (5) of the anhydride solutions were added in five 12 minutes intervals to the dissolved macromolecular compounds while the pH was maintained at 8.5. The final concentration of the acid anhydrides in the mixtures was 10 mg/ml. The mixtures were kept for another 1 hour at 25° C. and then extensively dialyzed against phosphate buffered saline (PBS) (0.15 M NaCl, 10 mM phosphate, pH 7.4). The dialyzed solutions were sterilized by filtration through 0.45 μm syringe filters (Acrodisc; Gelman Sciences, Ann Arbor, Mich.). In some cases, the modification procedure had to be modified because of problems with solubility of the reagents and/or the reaction products. In those cases, the reagents were dissolved in dimethyl sulfoxide (DMSO) and the reaction was carried out in 50% DMSO. Casein was first dissolved in 0.1 N NaOH and the pH was subsequently adjusted to pH 8.5. The modification of gelatin was carried out at pH 9.0 at final protein and reagent concentrations of 2.5 mg/ml, respectively. Treatment with 4-carboxybenzaldehyde was done in 0.1 M $NaHCO_3$ adjusted to pH 9.0. Treatment with 2,4,6-trinitrobenzenesulfonic acid (TNBS) was carried out at pH 9.0 in phosphate buffer for 3 hours at 25° C. and the reagent was originally dissolved in $H_2O$.

Some of the proteins treated to modify lysine residues were subsequently treated with phenylglyoxal specific for arginine (Lundblad, (1991)), *Chemical Reagents For Protein Modification,* CRC Press, Boca Raton, Fla. $NaHCO_3$ (8.4 mg/ml) was added to the modified proteins in PBS and the pH was adjusted to and maintained at 8.5. Phenylglyoxal (20 mg/ml) was added and the temperature was maintained at 37° C. for 2 hours. Subsequently, the mixture was dialyzed against PBS. In control examples, proteins whose lysines had not been modified were treated in the same way. In some experiments, treatments with acid anhydrides and phenylglyoxal were consecutive, omitting the intermediate dialysis step and addition of $NaHCO_3$.

BSA was reduced and alkylated as described in Neurath, A. R. and Strick, N., (1980), "Antibodies as Immunological Probes for Studying the Denaturation of HBsAg", *J. Med. Virol.,* 6, 309–322. BSA (20 mg/ml) was treated with trypsin (400 μg/ml) in 0.1 M phosphate pH 8.0 for 4 hours at 37° C. After addition of soybean trypsin inhibitor, the cleavage products were treated with trimellitic anhydride as described above and dialyzed using 500 M.W. cut-off membranes (Spectra/Por, Los Angeles, Calif.).

Protein concentrations were determined using the BCA Protein Assay Reagent Kit (Pierce). To quantitate lysine (terminal $NH_2$ groups) in the original and the chemically modified preparations, they were treated with TNBS as described above and dialyzed against 0.1 M $NaHSO_3$. The absorbances at 420 nm ($OD_{420}$) of the dialyzed preparations and their appropriate dilutions in 0.1 M $NaHSO_3$ were measured. The concentration of lysine was determined from calibration curves relating $OD_{420}$ values to lysine concentrations in standards.

Amino acid sequences of the proteins used were obtained from the PIR-International Protein Sequence Database (George, D. G., Barker, W. C., Mewes, H.-W., Pfeiffer, F., and Tsugita, A., (1994), "The-PIR-International Protein Sequence Database", *Nucl. Acids Res.* 22, 3569–3573). The net negative electric charges of the original and modified proteins were calculated by subtracting the sum of D+E residues from the sum of K+R residues present in each sequence, considering the extent of lysine modification and the introduction of additional negative charges by the respective chemical reagents. In the case of casein, phosphorylation of serines was considered in calculating the charges, and the mean charge of casein was calculated considering a composition of 65.7% α-, 19.3% β- and 15% κ-casein. The mean charge of milk proteins was calculated similarly, and is likely to be imprecise (casein represents ~80% of milk proteins) with an error of<±20%.

To prepare p-carboxyphenylglyoxal-treated bovine serum albumin (BSA), BSA at a final concentration of 20 mg/ml was dissolved in 0.1 M sodium carbonate buffer pH 8.5. The solution was warmed to 37° C. and 20 mg/ml of p-carboxyphenyl-glyoxal were added. After incubation for 2 hours at 37° C., the solution was dialyzed against PBS.

To prepare polyethyleneglycol (PEG)-conjugated 3-hydroxyphthalic anhydride-treated β-lactoglobulin (3HP-β-LG), 50 mg of an amino derivative of PEG(MW 3350; Sigma, St. Louis, Mo.) were activated using a 5-fold molar excess (=32.7 mg) of sulfosuccinimidyl 4-[N-maleimidomethyl]cyclohexane-1-carboxylate (SMCC; Pierce, Rockford, Ill.) at a pH 9 using the protocol provided by the manufacturer. The activated derivative containing thiol-reactive groups was separated from the excess of reagents by molecular exclusion chromatography on Sephadex G-10. The activated PEG collected in the void volume fractions was reacted with an equal amount (=mass) of 3HP-β-LG in the presence of 10 mM Tris(2-carboxyethyl)-phosphine for 3 hours at 25° C. By these procedures, the three cysteines present in 3HP-β-LG were expected to be modified by PEG. The final product was dialyzed against PBS.

Example 2

Measurement of Anti-HSV Activity

The inhibitory effect of 3HP-β-LG on HSV was measured by the following distinct methods.

In the first experiment, the cytopathic effect of HSV-1, strain MP [ATCC VR-735; obtained from the American Type Culture Collection (ATCC)] on HEP-2 cells was measured using a quantitative dye exclusion assays (using the dye 2,3-bis(2-methoxy-4-nitro-5-sulfophenyl)-2H-tetrazolium-5-carboxanilide inner salt ("XTT")) (N. W. Roehm, G. H. Rodgers, S. M. Hatfield, A. L. Glasebrook, "An Improved Colorimetric Assay For Cell Proliferation and Viability Using The Tetrazolium Salt XTT", *Journal of Immunological Methods,* 142, 257–265 (1990)). The $ED_{50}$ value for inhibition of HSV-1 infection was 0.39±0.06 μM and the $ED_{50}$ value (corresponding to 90% inhibition of virus infection) was 0.615±0.135 μM.

In a second method using the dye 3-(4,5-dimethylthiazo)-2-yl)-2,5-diphenyltetrazolium bromide ("MTT") (R. Pauwels, J. Balzini, M. Baba, R. Snoeck, D. Schols, P. Herdewijn, J. Desmyter and E. DeClercq, "Rapid and Automated Tetrazolium-Based Colorimetric Assay for The Detection of Anti-HIV Compounds", *Journal of Virological Methods,* 20, 309–321 (1988)). The $ED_{50}$ and $ED_{50}$ values were 0.19±0.001 and 0.267±0.002 μM, respectively.

In a further test, recombinant HSV virus was used which has the HSV gC promoter from nucleotide position from −110 to +71 linked to the lacZ coding sequences and which expresses high levels of β-galactosidase as a late HSV gene product (J. P. Weir, K. R. Steffy and M. Sethna, "An Insertion Vector for the Analysis of Gene Expression During Herpes Simplex Virus Infection", *Gene,* 81:271–274, (1990) in combination with Vero cells. In this system, virus replication was followed by determining β-galactosidase. Cells infected in the presence or absence of 3HP-β-LG were maintained for 24 hours at 37° C. Subsequently, the cells (200 μl of suspension) were lysed with 50 μl of 5% "TRITON X-100" containing protease inhibitors (phenylmethylsulfonyl fluoride, leupeptin and pepstatin all at 10 μg/ml). β-gal protein in 1:10 diluted lysates was quantitated using an ELISA kit from 5'→3' Inc. (Boulder, Colo.).

In additional tests, 3HP-β-LG was added to Vero cells 6 hours after infection instead of adding them to the cells at the same time as HSV was added. The results in the accompanying drawing (FIGURE) show that postponement of 3HP-β-LG addition by 6 hours had only a minor effect on anti-HSV activity, indicating that 3HP-β-LG can stop the replication of HSV in already infected cells.

In another assay system, ELVIS HSV cells commercially available from Diagnostic Hybrids, Inc., Athens, Ohio, were used in combination with HSV VR-735 from the ATCC. This cell line was derived from baby hamster kidney cells (BHK) cotransfected with a plasmid which contains the G418 antibiotic resistance marker and a plasmid which contains the *E. coli* lacZ gene placed behind an inducible HSV promoter from the HSV-1 UL39 gene which encodes ICP6, the large subunit of HSV ribo-nucleotide reductase (E. C. Stabell and P. D. Olivo, "Isolation of a Cell Line for Rapid and Sensitive Histochemical Assay for the Detection of Herpes Simplex Virus". *J. Virological Methods,* 38, 195–204, (1992). These cells were infected with HSV in the presence or absence of 3HP-β-LG. After 24 hours, β-galactosidase, the marker for productive HSV infection, was detected as described above. Results obtained using this assay, which are also included in the accompanying drawing, indicate that $ED_{50}$ values obtained by the two different methods differ by less than twofold. The results shown in the accompanying drawing appear similar to those obtained by detection of the cytopathogenic effect of HSV shown above.

Example 3

Testing the in vitro activity of a test compound against *Chlamydia trachmatis* growth on Human Cervical Epithelial Cells (HeLa 229)

Host Cells: HeLa 229 cells (ATCC #CCL 2.1) grown on glass coverslips in 24-well cell culture plates to about 80% confluency Chlamydia Strain: Chlamydia strain, LGV Type 1 (ATCC #VR-901 B)

Infectious Dose of Chlamydia used: 100 $TCID_{50}$ =$10^{-3}$ Dilution of Stock (LGV-1,P-3) in a volume of 0.5 ml Concentration of test compound used: 500 μg/ml, 250 μg/ml, 125 μg/ml Concentration of Positive control drug: Tetracycline used: 500 μg/ml, 250 μg/ml, 125 μg/ml Controls:

(1) Cell control: Cells only
(2) Chlamydia Control: Cells+$TCID_{50}$ of C. *trachomatis* in 0.5 ml volume
(3) Test Compound Control: Cells+test compound at concentrations of 500, 250, 125 μg/ml
(4) Positive Drug (Tetracycline) Control: Cells+Tetracycline at concentrations of 500, 250, 125 μg/ml Test Compound: 3-hydroxyphthalic anhydride modified bovine β-lactoglobulin.

A. Pretreatment of Hela 229 Cells with Test Compound

Pretreat cells with either the test compound or with the control drug tetracycline at concentrations of 500, 250, 125 μg/ml at 37° C. for 30 minutes and then infect with 100 $TCID_{50}$ of chlamydia trachomatis. Adsorb for one hour at 37° C. and then add medium (DMEM+5% FBS+1 μg/ml cycloheximide) containing 500, 250, 125 μg/ml of the test compound or tetracycline. Incubate at 37° C. for 3 days at 37° C. in a $CO_2$ incubator. Treat controls as set forth above.

B. Pretreatment of Chlamydia trachomatis with Test Compound

Pretreat 100 $TCID_{50}$ of chlamydia trachomatis with the test compound or tetracycline at concentrations of 500, 250, 125 μg/ml for 30 minutes at 37° C. and then infect cells and proceed as set forth above in the Pretreatment of HeLa 229 cells with the test compound.

C. Monitoring for C trachomatis infection (1) Microscopic observation of Cytopathic Effect (CPE)

(2) Giemsa staining to demonstrate inclusion and/or elementary bodies (3) Fluorescent antibody staining with Anti-MOMP monoclonal antibody against Chlamydia trachomatis (Chlamydia Direct FA reagent; DIFCO, Detroit, Mich.) to confirm inclusion and/or elementary bodies.

D. Summary of Results (1) Moderate to low degree of toxicity was observed with the test compound at concentrations of 500, 250, 125 μg/ml on HeLa 229 cells.

(2) Chlamydia trachomatis (100 $TCID_{50}$ ) replication was inhibited by the test compound at a concentration of 500 and 250 μg/ml, but not at a concentration of 125 μg/ml, as determined by the production CPE, Geimsa staining, and confirmation of the 500 and 125 μg/ml concentrations using fluorescent antibody staining by anti-MOMP Chlamydia trachomatis monoclonal antibody. Cell controls treated with the test compound were all negative.

(3) No difference was observed in the above observations between pretreatment of the HeLa cells or pretreatment of the Chlamydia trachomatis with the test compound.

(4) The control drug tetracycline used in the experiment completely inhibited the replication of Chlamydia trachomatis at concentrations of 500, 250, 125 [2 g/ml as observed using CPE, Geimsa staining, and confirmation of the 125 μg/ml concentration using fluorescent antibody staining by anti-MOMP chlamydia trachomatis monoclonal antibody. Cell controls treated with tetracycline were all negative.

The results are summarized in the following Tables.

TABLE 4

First Experiment
No DFA Staining

Pretreatment of Hela 229 Cells

| Controls | CPE | Geimsa | DFA |
|---|---|---|---|
| Cell Control | 0 | 0 | NT |
| | 0 | 0 | NT |
| Chlamydia Control | ++ | ++ | NT |
| | ++ | ++ | NT |

| | Cytopathic Effect | | | Geimsa Staining | | | Direct Fluorescent AB Staining | | |
|---|---|---|---|---|---|---|---|---|---|
| Test | 500 μg/ml | 250 μg/ml | 125 μg/ml | 500 μg/ml | 250 μg/ml | 125 μg/ml | 500 μg/ml | 250 μg/ml | 125 μg/ml |
| Test Compound + Chlamydia | 0 | 0 | + | 0 | 0 | + | NT | NT | NT |
| | 0 | 0 | + | 0 | 0 | + | NT | NT | NT |
| Test Compound only | 0 | 0 | 0 | 0 | 0 | 0 | NT | NT | NT |
| | 0 | 0 | 0 | 0 | 0 | 0 | NT | NT | NT |
| Tetracycline + Chlamydia | 0 | 0 | 0 | 0 | 0 | 0 | NT | NT | NT |
| | 0 | 0 | 0 | 0 | 0 | 0 | NT | NT | NT |
| Tetracycline only | 0 | 0 | 0 | 0 | 0 | 0 | NT | NT | NT |
| | 0 | 0 | 0 | 0 | 0 | 0 | NT | NT | NT |

LEGEND
++ = Abundant Chlamydia trachomatis replication
+ = Limited Chlamydia trachomatis replication
0 = No Chlamydia trachomatis replication
NT = Not Tested

TABLE 5

Second Experiment

Pretreatment of Hela 229 Cells

| Controls | CPE | Geimsa | DFA |
|---|---|---|---|
| Cell Control | 0 | 0 | NT |
| | 0 | NT | 0 |
| Chlamydia Control | ++ | ++ | NT |
| | ++ | NT | ++ |

| | Cytopathic Effect | | | Geimsa Staining | | | Direct Fluorescent AB Staining | | |
|---|---|---|---|---|---|---|---|---|---|
| Test | 500 μg/ml | 250 μg/ml | 125 μg/ml | 500 μg/ml | 250 μg/ml | 125 μg/ml | 500 μg/ml | 250 μg/ml | 125 μg/ml |
| Test Compound + Chlamydia | 0 | 0 | + | 0 | 0 | + | NT | NT | NT |
| | 0 | 0 | + | NT | 0 | NT | 0 | NT | + |
| Test Compound only | 0 | 0 | 0 | 0 | 0 | 0 | NT | NT | NT |
| | 0 | 0 | 0 | NT | 0 | NT | 0 | NT | 0 |

TABLE 5-continued

| | | | | | | | | | |
|---|---|---|---|---|---|---|---|---|---|
| | Second Experiment | | | | | | | | |
| Tetracycline + Chlamydia | 0 | 0 | 0 | 0 | 0 | 0 | NT | NT | NT |
| | 0 | 0 | 0 | NT | 0 | NT | 0 | NT | 0 |
| Tetracycline only | 0 | 0 | 0 | 0 | 0 | 0 | NT | NT | NT |
| | 0 | 0 | 0 | 0 | 0 | 0 | NT | NT | NT |

LEGEND
++ = Abundant Chlamydia trachomatis replication
+ = Limited Chlamydia trachomatis replication
0 = No Chlamydia trachomatis replication
NT = Not Tested

TABLE 6

Third Experiment

Pretreatment of Hela 229 Cells

| Controls | CPE | Geimsa | DFA |
|---|---|---|---|
| Cell Control | 0 | 0 | NT |
| | 0 | NT | 0 |
| Chlamydia Control | ++ | ++ | NT |
| | ++ | NT | ++ |

| | Cytopathic Effect | | | Geimsa Staining | | | Direct Fluorescent AB Staining | | |
|---|---|---|---|---|---|---|---|---|---|
| Test | 500 μg/ml | 250 μg/ml | 125 μg/ml | 500 μg/ml | 250 μg/ml | 125 μg/ml | 500 μg/ml | 250 μg/ml | 125 μg/ml |
| Test Compound + Chlamydia | 0 | 0 | + | 0 | 0 | + | NT | NT | NT |
| | 0 | 0 | + | NT | NT | NT | 0 | + | + |
| Test Compound only | 0 | 0 | 0 | 0 | 0 | 0 | NT | NT | NT |
| | 0 | 0 | 0 | NT | NT | NT | 0 | 0 | 0 |
| Tetracycline + Chlamydia | 0 | 0 | 0 | 0 | 0 | 0 | NT | NT | NT |
| | 0 | 0 | 0 | 0 | 0 | 0 | NT | NT | NT |
| Tetracycline only | 0 | 0 | 0 | 0 | 0 | 0 | NT | NT | NT |
| | 0 | 0 | 0 | 0 | 0 | 0 | NT | NT | NT |

LEGEND
++ = Abundant Chlamydia trachomatis replication
+ = Limited Chlamydia trachomatis replication
0 = No Chlamydia trachomatis replication
NT = Not Tested

TABLE 7

First Experiment
No DFA Staining

Pretreatment of Hela 229 Cells

| Controls | CPE | Geimsa | DFA |
|---|---|---|---|
| Cell Control | 0 | 0 | NT |
| | 0 | 0 | NT |
| Chlamydia Control | ++ | ++ | NT |
| | ++ | ++ | NT |

| | Cytopathic Effect | | | Geimsa Staining | | | Direct Fluorescent AB Staining | | |
|---|---|---|---|---|---|---|---|---|---|
| Test | 500 μg/ml | 250 μg/ml | 125 μg/ml | 500 μg/ml | 250 μg/ml | 125 μg/ml | 500 μg/ml | 250 μg/ml | 125 μg/ml |
| Test Compound + Chlamydia | 0 | 0 | + | 0 | 0 | + | NT | NT | NT |
| | 0 | 0 | + | 0 | 0 | + | NT | NT | NT |
| Test Compound only | 0 | 0 | 0 | 0 | 0 | 0 | NT | NT | NT |
| | 0 | 0 | 0 | 0 | 0 | 0 | NT | NT | NT |
| Tetracycline + Chlamydia | 0 | 0 | 0 | 0 | 0 | 0 | NT | NT | NT |
| | 0 | 0 | 0 | 0 | 0 | 0 | NT | NT | NT |
| Tetracycline only | 0 | 0 | 0 | 0 | 0 | 0 | NT | NT | NT |
| | 0 | 0 | 0 | 0 | 0 | 0 | NT | NT | NT |

LEGEND
++ = Abundant Chlamydia trachomatis replication
+ = Limited Chlamydia trachomatis replication
0 = No Chlamydia trachomatis replication
NT = Not Tested

TABLE 8

Second Experiment

Pretreatment of Hela 229 Cells

| Controls | CPE | Geimsa | DFA |
|---|---|---|---|
| Cell Control | 0 | 0 | NT |
| | 0 | NT | 0 |
| Chlamydia Control | ++ | ++ | NT |
| | ++ | NT | ++ |

| | Cytopathic Effect | | | Geimsa Staining | | | Direct Fluorescent AB Staining | | |
|---|---|---|---|---|---|---|---|---|---|
| Test | 500 μg/ml | 250 μg/ml | 125 μg/ml | 500 μg/ml | 250 μg/ml | 125 μg/ml | 500 μg/ml | 250 μg/ml | 125 μg/ml |
| Test Compound + Chlamydia | 0 | 0 | + | 0 | 0 | + | NT | NT | NT |
| | 0 | 0 | + | NT | 0 | NT | 0 | NT | + |
| Test Compound only | 0 | 0 | 0 | 0 | 0 | 0 | NT | NT | NT |
| | 0 | 0 | 0 | NT | 0 | NT | 0 | NT | 0 |
| Tetracycline + Chlamydia | 0 | 0 | 0 | 0 | 0 | 0 | NT | NT | NT |
| | 0 | 0 | 0 | NT | 0 | NT | 0 | NT | 0 |
| Tetracycline only | 0 | 0 | 0 | 0 | 0 | 0 | NT | NT | NT |
| | 0 | 0 | 0 | 0 | 0 | 0 | NT | NT | NT |

LEGEND
++ = Abundant Chlamydia trachomatis replication
+ = Limited Chlamydia trachomatis replication
0 = No Chlamydia trachomatis replication
NT = Not Tested

TABLE 9

Third Experiment

Pretreatment of Hela 229 Cells

| Controls | CPE | Geimsa | DFA |
|---|---|---|---|
| Cell Control | 0 | 0 | NT |
| | 0 | NT | 0 |
| Chlamydia Control | ++ | ++ | NT |
| | ++ | NT | ++ |

| | CPE | | | Geimsa | | | DFA | | |
|---|---|---|---|---|---|---|---|---|---|
| Test | 500 μg/ml | 250 μg/ml | 125 μg/ml | 500 μg/ml | 250 μg/ml | 125 μg/ml | 500 μg/ml | 250 μg/ml | 125 μg/ml |
| Test Compound + Chlamydia | 0 | 0 | + | 0 | 0 | + | NT | NT | NT |
| | 0 | 0 | + | NT | NT | NT | 0 | + | + |
| Test Compound only | 0 | 0 | 0 | 0 | 0 | 0 | NT | NT | NT |
| | 0 | 0 | 0 | NT | NT | NT | 0 | 0 | 0 |
| Tetracycline + Chlamydia | 0 | 0 | 0 | 0 | 0 | 0 | NT | NT | NT |
| | 0 | 0 | 0 | 0 | 0 | 0 | NT | NT | NT |
| Tetracycline only | 0 | 0 | 0 | 0 | 0 | 0 | NT | NT | NT |
| | 0 | 0 | 0 | 0 | 0 | 0 | NT | NT | NT |

LEGEND
++ = Abundant Chlamydia trachomatis replication
+ = Limited Chlamydia trachomatis replication
0 = No Chlamydia trachomatis replication
NT = Not Tested

TABLE 10

Interpretation of Results
Pretreatment of Hela 229 Cells

| Experiment | 500 μg/ml | 250 μg/ml | 125 μg/ml |
|---|---|---|---|
| Test Compound + Chlamydia | | | |
| First | Inhibitory | Inhibitory | Partially Inhibitory |
| First | Inhibitory | Inhibitory | Partially Inhibitory |
| Second | Inhibitory | Inhibitory | Partially Inhibitory |
| Second | Inhibitory | Inhibitory | Partially Inhibitory |

TABLE 10-continued

Interpretation of Results
Pretreatment of Hela 229 Cells

| Experiment | 500 μg/ml | 250 μg/ml | 125 μg/ml |
|---|---|---|---|
| Third | Inhibitory | Inhibitory | Partially Inhibitory |
| Third | Inhibitory | Moderately Inhibitory* | Partially Inhibitory |
| Tetracycline + Chlamydia | | | |
| First | Inhibitory | Inhibitory | Inhibitory |

TABLE 10-continued

| Interpretation of Results<br>Pretreatment of Hela 229 Cells | | | |
|---|---|---|---|
| Experiment | 500 $\mu$g/ml | 250 $\mu$g/ml | 125 $\mu$g/ml |
| First | Inhibitory | Inhibitory | Inhibitory |
| Second | Inhibitory | Inhibitory | Inhibitory |
| Second | Inhibitory | Inhibitory | Inhibitory |
| Third | Inhibitory | Inhibitory | Inhibitory |
| Third | Inhibitory | Inhibitory | Inhibitory |

* = C. trachomatis replication was detected ONLY by DFA staining, no CPE, no detection with Geimsa Staining

TABLE 11

| Interpretation of Result<br>Pretreatrnent of Chlamydia trachomatis | | | |
|---|---|---|---|
| Experiment | 500 $\mu$g/ml | 250 $\mu$g/ml | 125 $\mu$g/ml |
| Test Compound + Chlamydia | | | |
| First | Inhibitory | Inhibitory | Partially Inhibitory |
| First | Inhibitory | Inhibitory | Partially Inhibitory |
| Second | Inhibitory | Inhibitory | Partially Inhibitory |
| Second | Inhibitory | Inhibitory | Partially Inhibitory |
| Third | Inhibitory | Inhibitory | Partially Inhibitory |
| Third | Inhibitory | Moderately Inhibitory* | Partially Inhibitory |
| Tetracycline + Chlamydia | | | |
| First | Inhibitory | Inhibitory | Inhibitory |
| First | Inhibitory | Inhibitory | Inhibitory |
| Second | Inhibitory | Inhibitory | Inhibitory |
| Second | Inhibitory | Inhibitory | Inhibitory |
| Third | Inhibitory | Inhibitory | Inhibitory |
| Third | Inhibitory | Inhibitory | Inhibitory |

* = C. trachomatis replication was detected ONLY by DFA staining, no CPE, no detection with Geimsa Staining It will be appreciated that the instant specification is set forth by way of illustration and not limitation, and that various modifications and changes may be made without departure from the spirit and scope of the present invention.

We claim:

1. A method of preventing the transmission of or treating herpesvirus infection in a human comprising administering to a human an anti-herpesvirus effective amount of an anti-herpesvirus composition, either alone or in combination with a pharmaceutically acceptable carrier, the anti-herpesvirus composition comprising beta-lactoglobulin wherein at least one lysine or N-terminal amino acid group thereof is modified by an aromatic anhydride compound selected from the group consisting of trimellitic anhydride, trimellitic anhydride chloride and 3-hydroxyphthalic anhydride, wherein the aromatic anhydride compound used for modification of the beta-lactoglobulin is in an amount of 0.1 to 100 grams per gram of the beta-lactoglobulin.

2. The method of claim 1, wherein the aromatic anhydride compound is 3-hydroxyphthalic anhydride.

3. The method of claim 1, wherein the aromatic anhydride compound is trimellitic anhydride.

4. The method of claim 1, wherein the aromatic anhydride compound is trimellitic anhydride chloride.

5. The method of claim 1, wherein the aromatic anhydride compound used for modification of the beta-lactoglobulin is in an amount of 0.2 to 5 grams per gram of the beta-lactoglobulin.

6. The method of claim 1, wherein the herpesvirus is HSV.

7. The method of claim 1, wherein the herpesvirus is HSV-1.

8. The method of claim 1, wherein the herpesvirus is HSV-2.

9. The method of claim 1, wherein the herpesvirus is HSV-8.

10. The method of claim 1, wherein the herpesvirus is HCMV.

11. The method of claim 1, wherein the composition is topically administered.

* * * * *